US008467584B2

(12) United States Patent
Vija (10) Patent No.: US 8,467,584 B2
(45) Date of Patent: Jun. 18, 2013

(54) USE OF MULTIFOCAL COLLIMATORS IN BOTH ORGAN-SPECIFIC AND NON-SPECIFIC SPECT ACQUISITIONS

(75) Inventor: Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 437 days.

(21) Appl. No.: 12/885,759

(22) Filed: Sep. 20, 2010

(65) Prior Publication Data

US 2011/0096970 A1   Apr. 28, 2011

Related U.S. Application Data (60) Provisional application No. 61/254,042, filed on Oct. 22, 2009.

(51) Int. Cl.
*G06K 9/00* (2006.01)

(52) U.S. Cl.
USPC .......................................................... 382/128

(58) Field of Classification Search
None
See application file for complete search history.

(56) References Cited

U.S. PATENT DOCUMENTS

| 7,583,782 | B2 * | 9/2009 | Yamazaki ........................ 378/4 |
| 2006/0004275 | A1 * | 1/2006 | Vija et al. ...................... 600/407 |
| 2006/0025673 | A1 * | 2/2006 | De Leon et al. ............... 600/410 |
| 2009/0264753 | A1 * | 10/2009 | von Schulthess et al. .... 600/431 |

* cited by examiner

*Primary Examiner* — Tom Y Lu
(74) *Attorney, Agent, or Firm* — Peter Kendall (57) ABSTRACT

A method for obtaining nuclear medical images of a patient in which one or more first images are obtained. The one or more first images can be used to identify one or more regions of interest for subsequent images that focus on the regions of interest. The process can occur iteratively until it is determined, either by a physician or a computer program that sufficient images have been obtained to identify lesions or other pathology within a reasonable level of confidence.

15 Claims, 5 Drawing Sheets

USE OF MULTIFOCAL COLLIMATORS IN BOTH ORGAN-SPECIFIC AND NON-SPECIFIC SPECT ACQUISITIONS

RELATED APPLICATIONS

The present patent document claims the benefit of the filing date under 35 U.S.C. §119(e) of Provisional U.S. Patent Application Ser. No. 61/254,042, filed Oct. 22, 2009, which is hereby incorporated by reference.

BACKGROUND OF THE INVENTION

1. Field

The present disclosure relates generally to imaging systems and more particularly to imaging systems for use in nuclear medicine.

2. Description of Related Art

In a nuclear medicine imaging apparatus, a gamma or scintillation camera can obtain either planar images or Single Photon Emission Computed Tomography (SPECT) images, a collimator is mounted to the face of the imaging apparatus. The collimator is constructed of a dense, high-atomic-number material, such as lead. The material is bored with numerous tiny straight holes that allow radiation (e.g., gamma rays) to pass through. If the radiation is not traveling along the path of the hole, then the material absorbs it and it will not reach a detector of the nuclear imaging apparatus. The collimator thus collimates radiation before the radiation strikes a detector scintillation crystal. The radiation can be emitted from a distributed source (e.g., a radiopharmaceutical or radioisotope chosen for its affinity for a particular organ, tissue or region of the body) within a patient.

Figure 2:
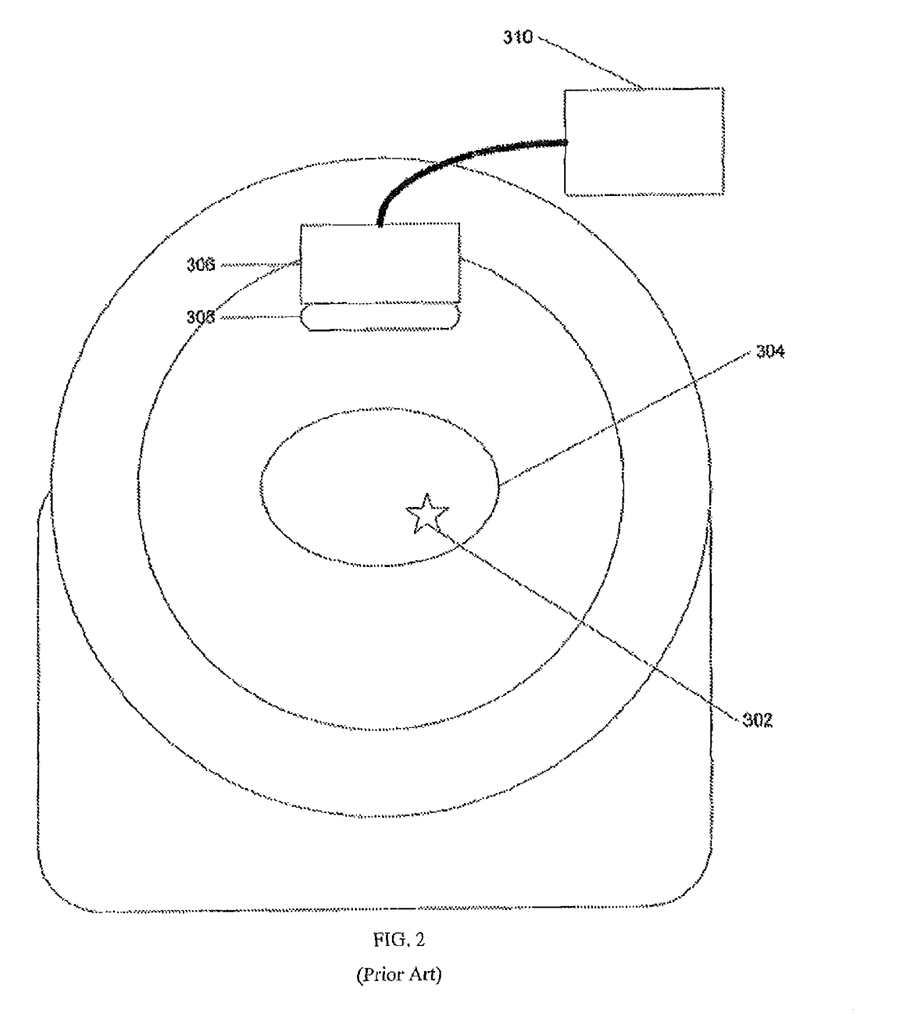
FIG. 2 is an illustrative block diagram of a nuclear system that is applicable to one embodiment of the present invention.

FIG. 2 is a block diagram of an exemplary SPECT or planar imaging apparatus. A radiation source 302 within an object to be imaged 304 (e.g., human body part) emits gamma photons that emanate from the object 304, pass through the collimator 308, and are captured by a scintillation detector 306, usually a large flat crystal of sodium iodide with thallium doping in a light-sealed housing, that converts the detected radiation into spatial incidence information. The system accumulates counts of gamma photons that are absorbed by the crystal in the detector 306. The crystal scintillates (i.e. emits low energy photons from the visible spectrum) in response to incident gamma radiation. An array of photomultiplier tubes (PMT) behind the crystal detects these fluorescent flashes and converts them into electrical signals. A computer 310 processes the electrical signals to determine energy and location of the incident photons and stores that incidence information along with other relevant information as the projection data. The computer 310 can then also display the projection data as two dimensional images of the relative spatial count density or distribution for each acquired view on a monitor. These images then reflect the distribution and relative concentration of radioactive tracer elements present in the organs and tissues imaged. The individual two-dimensional images are also referred to as planar images because the depth information has been lost as they are taken from only one angle. The computer can then use projection data from a number of different viewing angles to reconstruct the volumetric (3d or 4d) distribution of the injected radioisotope, essentially restoring the lost depth information from the planar views by processing the plurality of planar views which have to fulfill certain tomographic criteria. This process is also called tomographic reconstruction.

A non-parallel hole collimator, such as a variable focus collimator, can be designed to magnify a specific organ onto the detector face yet to avoid truncation of the surrounding body. The non-parallel hole collimator thus allows for gain in count sensitivity, as measured by the reduction in dose or acquisition time needed to complete the clinical task with the same clinical sensitivity and specificity. Typically the target organ has to be at some specific distance to be in focal area depending on the collimator design and desired magnification. This distance is to be maintained to achieve better performance, reduce acquisition time and reduce dose. The key properties of such a collimator design has to be that it changes magnification both when object-collimator distance is changed, and when an object is moved parallel to the collimator surface. A simple fan-beam collimator is not suitable to achieve such requirements.

The variable focal collimator is used in cardiac imaging where a single organ is examined within the field of view (FOV) of the detector. The image of the single organ has a more or less enlarged projection image depending on the collimator properties and distance to the object. This magnification could provide an increase in sensitivity, allowing for the reduction of acquisition time and/or dose. Current methods of Planar or SPECT imaging do not provide sufficiently sensitive results, particularly when scanning over a large area, such as an entire body in a scan of the skeletal system as it is done in oncology imaging. More sensitive results would result in more accurate diagnosis of pathology such as tumors. To obtain sensitive images, multiple scans can be made using the same or different imaging apparatuses, which can require a patient to move from one apparatus to another which causes delay, increases costs, is cumbersome, and has lower specificity and sensitivity. Additionally, the multiple apparatuses are not optimized and therefore still result in lower image quality.

SUMMARY OF THE INVENTION

Embodiments of the present invention can perform multiple scans of a subject, iteratively and efficiently, to identify one or more regions of interest and to diagnose pathology in the subject. To obtain optimal results using a non-parallel hole collimator, the region of interest should be within the focus of the collimator. In typical scans, the region of interest would be a predetermined area of the body such as a heart. In full body scans, there is no particular region of interest because the entire body is scanned. The image resulting from a first pass of the scanner yields valuable medical information to assess the overall state and extent of the disease, but it also indicates regions that should be looked at more closely, i.e., regions of interest. These regions can subsequently be examined in more detail by placing them within the focus of the collimator. This will allow for more counts to be collected for a given time compared to parallel hole collimator, resulting in higher statistical power of the tomographic data of this ROI and using a computer resulting in a better detectable and interpretable lesion—in short in a clearer image. After obtaining a clearer image, additional diseased areas may be observed adjacent to the regions of interest, which can then be scanned in another iteration.

According to one embodiment, a subject is injected with, for example, a radioisotope and is imaged with a gamma camera. Using a variable focal collimator, two or more images can be made of the subject at different locations. The images are then examined to determine regions of interest to be examined further. A second iteration is performed to take additional images having a greater number of counts. Additional iterations can be performed as desired to increase accuracy and complete an examination of the subject. The subsequent iterations allow for increased counts to be obtained from the regions of interest, sensitivity, specificity and more accurate diagnosis. The different iterations can be performed with the same apparatus but at different configurations and orbits using different cameras or collimators.

A variable of multifocal collimator (VFC or MFC) as intended and designed for imaging specific organs, such as the heart, brain or liver, can also be used in non-organ specific applications, such as a typical bone SPECT. In one embodiment, an entire body or a rather large portion of the body is scanned to identify and categorize suspicious regions of interest (higher than typical tracer uptake, indicative of inflammation or cancer).

Further, in this embodiment, a non-parallel hole collimator can perform non-organ specific scanning, such as in bone SPECT, and can improve the ability to detect smaller lesions contrast than typically possible. The idea can then readily be extended to other types of collimators with similar properties, namely collimators having a non-stationary response to a point source across the detector face, even when the distance is held constant, such as in the most general case: coded apertures, pinholes, slit-slat or any combination thereof. This disclosure focuses on using diagnostic imaging to identify or reject regions of interest ("detection task") with improved confidence. However, with appropriate data, calibration and reconstruction methods the task of quantification is also possible. This embodiment can be used to diagnose disease, and to plan and monitor treatment.

DETAILED DESCRIPTION OF THE INVENTION

The following description is presented to enable any person skilled in the art to use a method to efficiently produce superior reconstructed images using, for example, planar imaging or Single Photon Emission Computed Tomography (SPECT). Various modifications to the preferred embodiments will be readily apparent to those skilled in the art, and the generic principles defined herein may be applied to other embodiments and applications without departing from the spirit and scope of the present disclosure. In the following description, numerous details are set forth for the purpose of explanation. However, one of ordinary skill in the art will realize that the present disclosure might be practiced without the use of these specific details. To more efficiently illustrate and describe embodiments of the present disclosure, identical reference numerals are used in the specification and drawings to identify parts that are essentially the same in different stages, versions or instantiations of such parts shown in the drawings. Thus, the present disclosure is not intended to be limited to the embodiments shown, but is to be accorded the widest scope consistent with the principles and features disclosed herein.

Figure 1:
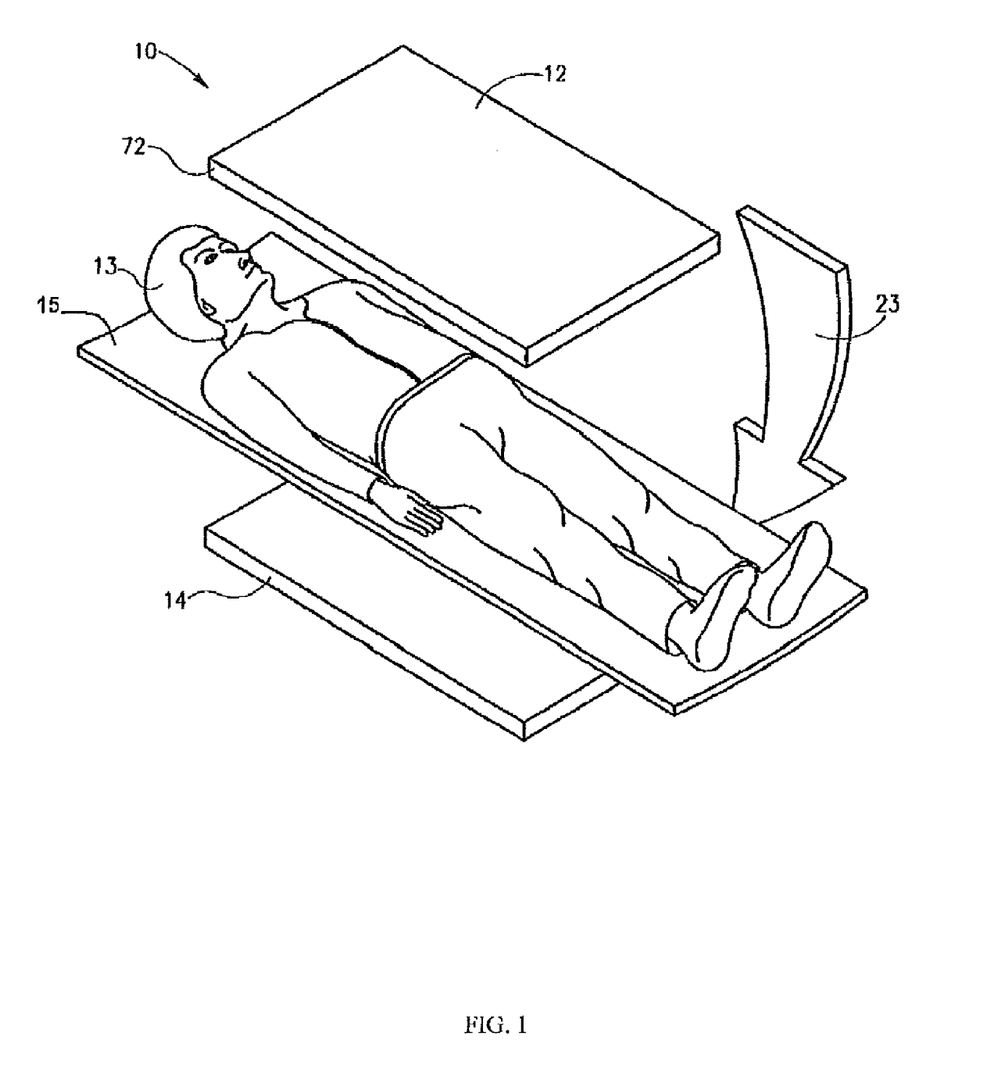
FIG. 1 is an illustrative representation of a patient inside a nuclear imaging apparatus in accordance with one embodiment of the present invention.

FIG. 1 depicts an exemplary embodiment of a patient 13 on a patient bed 15 inside a nuclear imaging apparatus 10. Two collimators, 12 and 14, are located around the patient 13. The collimators 12 and 14 collimate radiation from the patient to be imaged. The collimated radiation is detected using a crystal (not shown) which scintillates in response to incident gamma radiation. The collimators 12 and 14 may rotate around the patient as shown by arrow 23. The collimators 12 and 14 may also shift or swivel. In addition, the patient bed 15 may be capable of moving by rotating, shifting, or swiveling. The motion of the patient bed 15 and/or the collimators 12 and 14 facilitates taking images of the patient 13 from different angles and orientations. In accordance with the present disclosure, a non-parallel hole (e.g., multifocal) collimator can be used to acquire incidence information from radiation emanating from a subject, such as a patient at multiple orientations.

Figure 3:
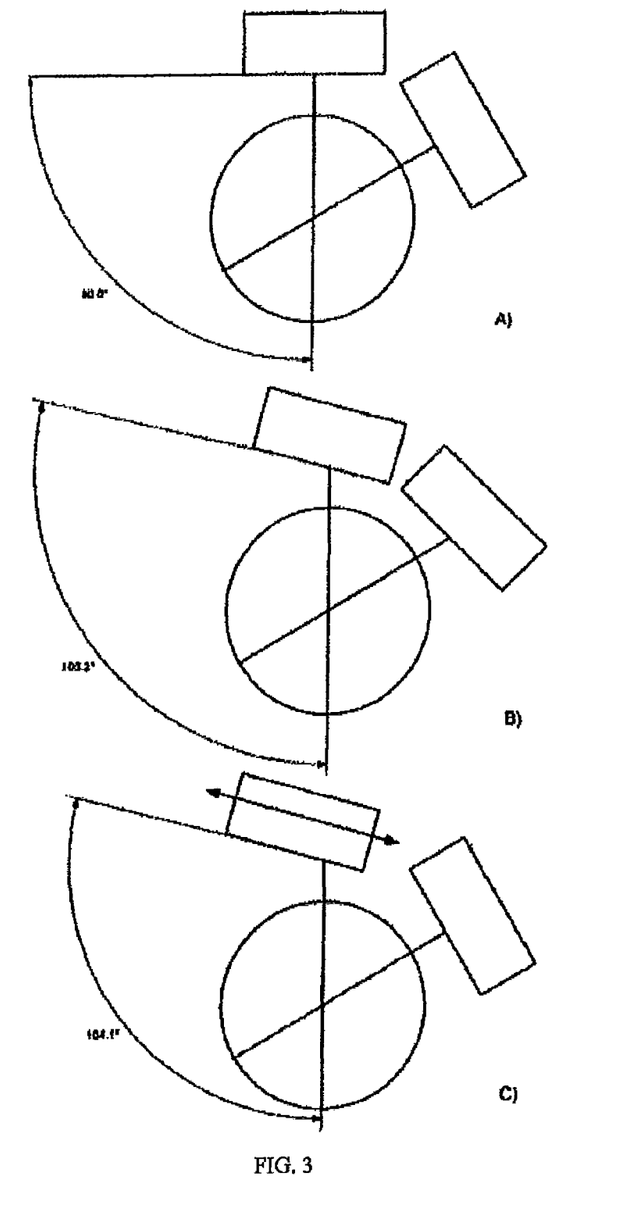
FIG. 3 is an illustrative representation of the possible types of detector motion around a gantry center in accordance with one embodiment of the present invention.

FIG. 3 depicts examples of possible detector movements. Each of the three diagrams illustrates the motion of one detector with respect to the center of the gantry. The top example, labeled A, depicts the collimator/detector rotating around a gantry center. The center example, labeled B, depicts the collimator/detector swiveling around its central axis in addition to rotation about the gantry center. Finally, the bottom example, labeled C, depicts the collimator/detector shifting or translating the detector center with respect to the gantry center, in addition to rotation about the gantry center and swiveling about the detector central axis. The motions may occur independently or concurrently.

Figure 4:
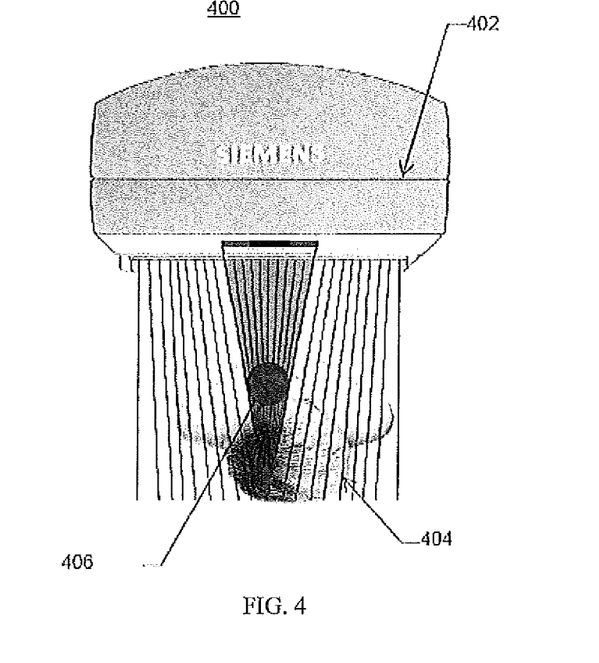
FIG. 4 is an illustration of a subject in an imaging apparatus in accordance with one embodiment of the present invention.

FIG. 4 illustrates an exemplary imaging apparatus 400 comprising collimator 402 having a focus for scanning patient 404. The focus is focused on a region of interest 406, which could be, for example, a tumor of the left lung. The collimator 402 can be used to decrease acquisition time by sampling incidence information from the region of interest at about twice the rate than one collimator could.

Information about the depth of a region of interest can be garnered from information about the difference between two images. This is described in U.S. Provisional Application No. 61/097,925, which is hereby incorporated by reference in its entirety. For the purposes of this disclosure, the depth information can be used to focus the collimator on the region of interest, thereby obtaining a focused image with greater quality.

In one embodiment, a scan can be performed to acquire incidence information from the entire subject, such as a patient or organ, using a non-parallel hole collimator that can be moved in a body-contoured or peanut-shaped orbit. Using a body-contoured orbit minimizes truncation and the projection is essentially parallel. In another embodiment, incidence information can be acquired by performing a planar scan of the entire subject. This can be done using a parallel-hole collimator or an MFC that is at a short distance from the subject, thereby acting similarly to a parallel-hole collimator because the subject is not in the foci of the collimator and therefore produces a substantially planar image. A first scan can take about 20 minutes. In other embodiments, a spiral tomographic scan can be performed, which can be faster than the planar scan.

Next, a first image can be reconstructed to generate an image estimating the activity distribution. This image can be presented for interpretation to a physician with or without a computer-aided diagnosis (CAD) capability. The physician can perform a lesion detection task, i.e., identify all, or all marginal or potential lesions. The physician can identify by marking one or more locations on the image displayed on an interactive display, and rank them according some confidence ranking (e.g., a scale from 1-5, with 5 being sure it is a lesion and 1 is not sure at all (i.e., guessing) that this indeed is or is not a lesion. The interactive display can be, for example, a touch screen that the physician can use a stylus or finger to identify regions of interest. The interactive display can be communicatively coupled to a processor, which processes marks made by the physician to identify the regions of interest. Finally, the 3D locations and rankings can be recorded in a list in memory.

In other embodiments, the procedure can be substantially the same, but a computer program can replace the physician in the lesion detection task. The computer program can detect lesions using an automated method, for example, areas having greater incidence of gamma radiation can be assumed to contain lesions, and therefore may be of interest for further examination.

After determining the regions of interest, the computer device can compute, based on the 3D locations, ranking, and known non-parallel hole collimator design parameters, a general scan orbit that includes rotation about the regions of interest at some distance or an axial or transaxial translation. In the simplest case, only one lesion or region of interest is examined more closely. The detectors and non-parallel hole collimator could be centered to rotate about the region of interest keeping the region of interest in the focal point of magnification at some distance trading off magnification, system limitations, patient habitus limitations and resolution. This orbit (start and end angle, angular step, radius at each angular step) could be determined by an algorithm or a predetermined Lookup Table (LUT), other similar algorithms can be used without deviating from this disclosure. The region of interest is now magnified, and based on the specific ranking given by the physician, the acquisition time and dwell time per view can be determined. For example, regions of interest with higher rankings, i.e., more certainty that they are lesions, can be examined more quickly, or even not at all, because there is more certainty that they are lesions.

Instead of scanning each region of interest in a random order, the system can pre-compute a more optimal orbit to acquire incidence information from all regions of interest, focusing on each of them. In more complex cases, three or more regions of interest can be identified either by a physician or a computer algorithm. In these cases, in addition to determining a scan orbit for each region of interest as described above, a shortest path to traverse all regions of interest can be determined to minimize total acquisition time. This problem is known as the "traveling salesman problem." Well-known algorithms, such as branch-and-bound algorithms, can be used to solve this problem. Determining a shortest path can save time relative to simply traversing an unprocessed list of regions of interest. Finding the shortest path is more efficient than traversing a random path. That is, the shortest path is more efficient because it can reduce the amount of radio isotope injected, and reduce acquisition time leading to improved patient service and increasing the number of scans that can be performed in a day. Therefore, costs can efficiently be reduced and more scans can be performed leading to more income.

After determining a path, the imaging apparatus can acquire second incidence information or more counts from the regions of interest. A reconstruction algorithm can take all the acquisition orbit parameters and MFC characteristics into consideration to generate one or more second images, which are focused on that region(s) of interest, presenting the physician or computer program this new image for interpretation. The incidence information can be obtained from the regions of interest by placing them in the focus area of the MFC, thereby reducing the signal-to-noise ratio. These second images can be obtained using normal SPECT and can take 20-40 minutes, or, a full SPECT scan be performed taking approximately 60-100 minutes. The second image(s) can be presented for identification singularly or combined, with or without the first image. It can be advantageous to combine all of the images together with the first image to help the physician keep track of individual lesions. However, in the embodiment using a computer algorithm for identification, combining the images may not be as beneficial. The identification and ranking may now have improved the confidence score, marking the lesions now as either absent or present with a high enough confidence. In addition, other proximal regions of interest may now be more readily identified, localized, and ranked and system readied for another focusing study.

This process can continue until the physician or computer program determines that all lesions are reasonably well identified with the needed confidence. This can occur in one or more iterations. Of course, in other embodiments, a computer program can perform initial lesion identification and a physician can modify the computer program's identification. In still further embodiments, a computer program can perform all of the identification and a physician may only examine the results after all images are reconstructed; then, the physician can request additional acquisitions and reconstruction.

Some embodiments can include use of different pairs of collimators with different characteristics, including parallel-hole and fan beam collimators. Similarly, more general collimators can be used, such as coded apertures, pinholes, and pinhole arrays, slit slat and so on, all having in common the ability to improve count sensitivity at some specific orbit.

Still further embodiments can use registered Computerized Tomography (CT) data to provide accurate localization information to the system for the second focusing scan. The CT data could come from a hybrid SPECT/CT system, where the registration accuracy could be very good. It could also come from a standalone CT, using different software.

Other embodiments can use registered Magnetic Resonance (MR) data to provide accurate localization information to the system for the subsequent focusing scan. The MR data could come from a hybrid SPECT/MR system, where the registration accuracy could be very good. It could also come from a standalone MR, using different software, e.g., a brain examination, where MR data is often available.

In some embodiments, use of registered ultrasound (US) data can provide accurate focalization information to the system for the subsequent focusing scan. The US data could come from a hybrid SPECT/US system, where the registration accuracy could be very good. It could also come from a standalone US, using different software, e.g., a prostate examination, where intrarectal US is common).

Any combination of the aforementioned anatomical modalities is also possible. In some cases, additional data from a functional modality, such as Positron Emission Tomography (PET) using, for example, flurodeoxyglucose or NaF, which can be used to guide the SPECT focusing scan.

The ability to use a combination of different imaging techniques together or separately increases the versatility of the imaging apparatus, thereby decreasing the number of beds needed to perform different scans. This can be particularly valuable for rural facilities that desire a diverse range of imaging options but that do not want to purchase a separate bed for each type of scan. Combining different scanning alternatives in the same imaging apparatus not only can increase the accuracy of diagnosis, but can save space, time and money.

Some embodiments can use SPECT data from a previous scan. These embodiments can monitor treatment, whereby registration to a scan at a former time the lesion is set to the focal point. It is can be advantageous in this application to estimate the reconstructed image volume in units of kBq/ml or similar, such that the different images are calibrated the differences between the regions if interest are quantified.

Another extension is to use SPECT data from a previous scan, say before commencement of therapy. This application then extends to treatment monitoring, whereby registration to a scan at a former time the lesion in question is set to be at the focal point, and the acquisition is performed as previously described. The estimated image volume can be reconstructed in units of kBq/ml or similar (i.e. calibrated and thus quantitative). The specific orbit for each lesion or cluster of regions of interest can stored and recalled and repeated if needed. This is useful when the application is used for treatment monitoring. Accuracy demands is in the order of 1 to 2 pixels (radius of accuracy sphere), since the area in focus is typically much larger. Demand on precision is as high as motion control detector movements, thus much tighter typically in the order of tenths of mm and tenths of degrees.

Figure 5:
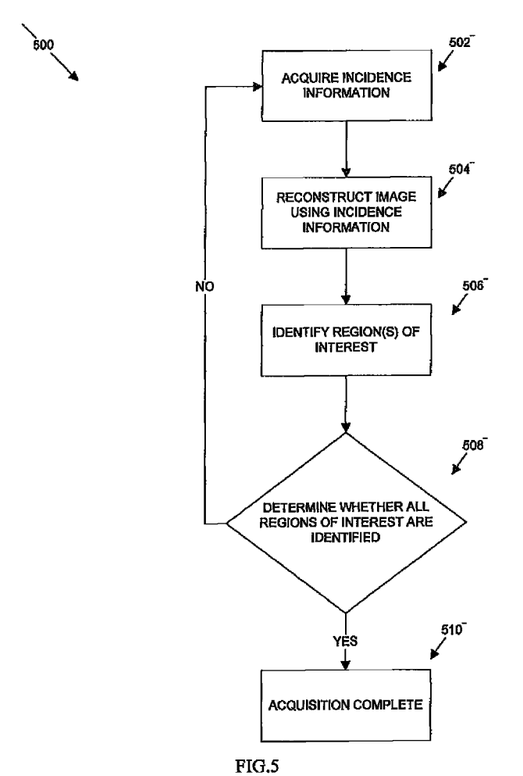
FIG. 5 is an illustrative flow chart of a method for obtaining an image of a subject using nuclear imaging in accordance with one embodiment of the present invention.

FIG. 5 illustrates a flowchart 500 of steps for identifying lesions in accordance with one exemplary embodiment using nuclear imaging, but, as described above, other embodiments are contemplated using different modalities such as US, X-ray, PET, MT, CT and any combination thereof. The first step 502 in the exemplary embodiment is to acquire first incidence information. In the second step 504, an image is reconstructed using the incidence information. The image can then be presented to a physician, or input to a computer program, for identification of regions of interest, e.g., regions containing possible lesions. In step 508, either the physician or the computer program determines whether additional incidence information needs to be acquired to reconstruct more images. If so, steps 502-508 can be repeated to acquire more counts; else, image acquisition is completed in step 510, which can mean that all lesions have been identified to the satisfaction of the physician or the computer program.

Embodiments within the scope of the present disclosure can also include tangible and/or non-transitory computer-readable storage media for carrying or having computer-executable instructions or data structures stored thereon. Such non-transitory computer-readable storage media can be any available media that can be accessed by a general purpose or special-purpose computer, including the functional design of any special-purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special-purpose computer, or special-purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other embodiments of the disclosure may be practiced in network computing environments with many types of computer system configurations, including personal computers, hand-held devices, multi-processor systems, microprocessor-based or programmable consumer electronics, network PCs, mini-computers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Those of ordinary skill may vary the data collection apparatus and methods for recording and processing the images without varying from the scope of the present invention as defined in the appended claims.

I claim:

1. A method of reconstructing a tomographic image using a nuclear imaging apparatus having a non-parallel hole collimator comprising:

acquiring, by a gamma camera, first incidence information from a radiation field radiating from a subject;

reconstructing, by a processor, the first incidence information to generate a first image;

identifying, by the processor, one or more regions of interest in the first image;

focusing, by the non-parallel hole collimator, on at least one of the regions of interest;

acquiring, by the processor, second incidence information from the radiation field; and reconstructing, by the processor, the second incidence information to generate a second image, wherein the second image has a higher number of counts than the first image.

2. The method according to claim 1 further comprising:

performing, until no more regions of interest are identified, the following steps comprising:

identifying, by the processor, additional regions of interest;

acquiring, by the gamma camera, additional incidence information focused on at least one of the additional regions of interest; and reconstructing, by the processor, at least one additional image of the at least one additional region of interest until a final image is reconstructed.

3. The method according to claim 1 further comprising determining, by the processor, an order and path for acquiring incidence information from three or more regions of interest to be focused on, wherein the order and path are chosen to be more efficient than an average of randomly selected orders and paths.

4. The method according to claim 1, wherein the first image is substantially planar and the second image focuses on at least one of the regions of interest.

5. The method according to claim 1 further comprising determining, by the processor, depth information of at least one of the regions of interest; and
using, by the imaging apparatus, the depth information to focus on at least one of the regions of interest.

6. The method according to claim 1 further comprising registering, by the processor, the first and second images.

7. The method according to claim 2 further comprising registering, by the processor, one or more of the previously reconstructed images.

8. A system for reconstructing images of a subject comprising:
a nuclear imaging detector for acquiring first incidence information;
a processor for reconstructing the first incidence information into a first image of the subject; and
an interactive display communicatively coupled to the processor, wherein the processor causes display of one or more images of the subject to the interactive display to identify one or more regions of interest, wherein the processor further causes the nuclear imaging detector to focus on at least one of the regions of interest and acquire second incidence information, and the processor further reconstructs a second image using the second incidence information, wherein the second image has a higher number of counts than the first image, wherein the nuclear imaging detector focuses on the regions of interest via a planar collimator and a multi-focal collimator.

9. A non-transitory computer-readable storage medium storing instructions which, when executed by a computing device, cause the computing device to perform steps for reconstructing a tomographic image using a nuclear imaging apparatus having a non-parallel hole collimator comprising:
acquiring first incidence information from a radiation field radiating from a subject;
reconstructing the first incidence information to generate a first image;
identifying one or more regions of interest in the first image;
focusing on at least one of the regions of interest;
acquiring second incidence information from the radiation field; and
reconstructing the second incidence information to generate a second image, wherein the second image has a higher number of counts than the first image.

10. The computer-readable medium according to claim 9 further comprising:
performing, until no more regions of interest are identified, the following steps comprising:
identifying additional regions of interest;
acquiring additional incidence information focused on at least one of the additional regions of interest; and
reconstructing at least one additional image of the at least one additional region of interest until a final image is reconstructed.

11. The computer-readable medium according to claim 9 further comprising determining an order and path for acquiring incidence information from three or more regions of interest to be focused on, wherein the order and path are chosen to be more efficient than an average of randomly selected orders and paths.

12. The computer-readable medium according to claim 9, wherein the first image comprises a substantially planar image of the subject and the second image focuses on at least one of the regions of interest.

13. The computer-readable medium according to claim 9 further comprising determining depth information of at least one of the regions of interest; and
using the depth information to focus on at least one of the regions of interest.

14. The computer-readable medium according to claim 9 further comprising registering, by the processor, the first and second images.

15. The computer-readable medium according to claim 10 further comprising registering one or more of the previously reconstructed images.

* * * * *